(12) United States Patent
Matsuzawa et al.

(10) Patent No.: US 9,476,023 B2
(45) Date of Patent: Oct. 25, 2016

(54) CULTURE DEVICE

(75) Inventors: Yoshiaki Matsuzawa, Tokyo (JP); Kousuke Ishii, Tokyo (JP); Hiroshi Tanaka, Tokyo (JP); Junji Yamamura, Tokyo (JP)

(73) Assignee: IHI CORPORATION (JP)

( * ) Notice: Subject to any disclaimer, the term of this patent is extended or adjusted under 35 U.S.C. 154(b) by 191 days.

(21) Appl. No.: 14/232,738

(22) PCT Filed: Jul. 27, 2012

(86) PCT No.: PCT/JP2012/069224
§ 371 (c)(1),
(2), (4) Date: Jan. 14, 2014

(87) PCT Pub. No.: WO2013/015422
PCT Pub. Date: Jan. 31, 2013

(65) Prior Publication Data
US 2014/0147915 A1    May 29, 2014

(30) Foreign Application Priority Data

Jul. 27, 2011 (JP) .................................. 2011-163868

(51) Int. Cl.
*C12M 1/107* (2006.01)
*C12N 1/12* (2006.01)
(Continued)

(52) U.S. Cl.
CPC ................ *C12N 1/12* (2013.01); *C12M 21/02* (2013.01); *C12M 23/18* (2013.01); *C12M 23/36* (2013.01); *C12M 23/48* (2013.01)

(58) Field of Classification Search
CPC ..... C12M 21/02; C12M 23/18; B65D 88/48; E04H 15/22; A01G 9/1407; A01G 9/1415; A01G 33/00
See application file for complete search history.

(56) References Cited

U.S. PATENT DOCUMENTS 5,815,991 A * 10/1998 de Ridder ............ A01G 9/1407
                                                              135/115
2006/0118136 A1 * 6/2006 Manor .................... A47L 11/38
                                                              134/6
(Continued)

FOREIGN PATENT DOCUMENTS

JP        54-086689        7/1979
JP        05-168463        7/1993
(Continued)

OTHER PUBLICATIONS

International Search Report and Written Opinion mailed Oct. 9, 2012 in corresponding PCT International Application No. PCT/JP2012/069224.

(Continued)

*Primary Examiner* — William H Beisner
(74) *Attorney, Agent, or Firm* — Ostrolenk Faber LLP (57) ABSTRACT

The culture device (100, 200) for culturing algae includes a culture pond (110) including an opening (112) on an upper side thereof and accommodating an alga solution (M) as a culture solution containing algae; a sheet (130) having optical transparency and flexibility, the sheet sealing at least a portion of the opening (112) of the culture pond (110); and a gas supply unit (124, 160, 212) used to supply high concentration $CO_2$ gas having a higher concentration of carbon dioxide than that of the atmosphere, between the culture pond (110) and the sheet (130). A gas storage space (G) to store gas between a liquid surface (114) of the alga solution (M) and the sheet (130) is formed by at least part of the supplied high concentration $CO_2$ gas.

7 Claims, 5 Drawing Sheets

(51) Int. Cl.
  *C12M 1/00* (2006.01)
  *C12M 3/00* (2006.01)

(56) References Cited

U.S. PATENT DOCUMENTS

| | | | |
|---|---|---|---|
| 2008/0155890 A1* | 7/2008 | Oyler | A01G 33/00 47/1.4 |
| 2008/0178739 A1 | 7/2008 | Lewnard | 95/186 |
| 2011/0258920 A1* | 10/2011 | Licamele | A01G 33/00 47/1.4 |

FOREIGN PATENT DOCUMENTS

| | | |
|---|---|---|
| JP | 05-184347 | 7/1993 |
| JP | 05-184348 | 7/1993 |
| JP | 08-173139 | 7/1996 |
| JP | 09-057058 | 3/1997 |

OTHER PUBLICATIONS

Orlando Jorquera et al., "Comparative energy life-cycle analyses of microalgal biomass production in open ponds and photobioreactors," Elsevier, Bioresource Technology 101 (2010): pp. 1406-1413.
Japanese Office Action, dated Dec. 9, 2014, issued in corresponding Japanese Patent Application No. 2013-525785. Included English Translation. Total 6 pages.
European Search Report, dated Jun. 18, 2015, issued in corresponding European Patent Application No. 12816847.3. Total 6 pages.

* cited by examiner

CULTURE DEVICE

CROSS-REFERENCE TO RELATED APPLICATIONS

The present application is a 35 U.S.C. §371 national phase conversion of PCT/JP2012/069224, filed Jul. 27, 2012, which claims priority to Japanese Patent Application No. 2011-163868, filed Jul. 27, 2011, the contents of which are incorporated herein by reference. The PCT International Application was published in the Japanese language.

TECHNICAL FIELD

The present invention relates to a culture device which cultures algae or the like.

Priority is claimed on Japanese Patent Application No. 2011-163868, filed Jul. 27, 2011, the contents of which are incorporated herein by reference.

BACKGROUND ART

In recent years, algae (in particular, microalgae) which can produce a physiologically active substance such as a biofuel (hydrocarbon or bio-diesel) and astaxanthin have attracted attention. A technology has been studied in which such algae are cultured in large quantity and products thereof are used as substitute energy sources for oil or are used to produce drugs, cosmetics, foods, or the like.

A culture device for large-scale culture of algae or the like includes a culture device in which a water surface of a culture solution is exposed to the atmosphere (open system reactor), for example, a raceway type or open pond type culture device (culture pond) (for example, refer to Non-Patent Document 1). Plants, such as the algae, photosynthesize by using carbon dioxide ($CO_2$) as a carbon source under a condition of light irradiation so as to proliferate or to produce products such as hydrocarbons. Therefore, in order to improve the production efficiency of the products such as the biofuel and the physiologically active substance, it is desirable to allow light to reach inside the culture pond and to sufficiently dissolve carbon dioxide into the culture solution through bubbling supply.

In the raceway type culture device, there is a trade-off relationship between allowing light to reach inside the culture pond and dissolving carbon dioxide into the culture solution using the bubbling supply or the like.

To be more specific, in the raceway type culture device, the light enters inside the culture pond only from the water surface. Thus, if the algae proliferate, the algae block the light themselves, whereby the reaching distance of the light may be shortened, and the efficiency of photosynthesis of the algae may be deteriorated. Therefore, the raceway type culture device is formed to be shallow to some degree (for example, approximately 30 cm) so that the light reaches a bottom surface of the culture pond even if the algae proliferate.

However, if a depth (vertical length) of the culture pond is shortened in view of the light reaching, even if the carbon dioxide is supplied into the culture solution using the bubbling supply or the like, the supplied carbon dioxide may be immediately released to the atmosphere from the water surface. Thus, it may not possible to ensure time for contact between the carbon dioxide and the culture solution, thereby causing insufficient dissolving of the carbon dioxide into the culture solution. In addition, a concentration of the carbon dioxide dissolved into the culture solution generally varies until the concentration reaches equilibrium with a concentration of the carbon dioxide in the atmosphere. Thus, even if the culture pond is supplied with the culture solution in which the carbon dioxide is dissolved in advance so as to have a high concentration (for example, approximately 2% to 3%), since the raceway type culture device has the water surface exposed to the atmosphere, the concentration of the carbon dioxide dissolved into the culture solution is decreased to the concentration of the carbon dioxide in the atmosphere (approximately 400 ppm) in a short period of time.

Therefore, a technology is disclosed which separately includes a culture device which dissolves high concentration carbon dioxide into an alga solution as the culture solution containing algae; and a culture pond which accommodates the alga solution having the dissolved high concentration carbon dioxide and delivered from the culture device and in which the photosynthesis of the algae is performed (for example, refer to Patent Document 1). In the technology disclosed in Patent Document 1, a box-shaped cover member (lid) composed of plate-shaped members made of vinyl resin or acrylic resin is installed on an outer edge of the culture pond, thereby covering an opening of the culture pond, and thus the carbon dioxide in the culture pond is prevented from being released to the atmosphere.

DOCUMENT OF RELATED ART

Patent Document

[Patent Document 1] Japanese Unexamined Patent Application, First Publication No. H08-173139

Non-Patent Document

[Non-Patent Document 1] Elsevier, Bioresource Technology 101, 2010: Pages 1406 to 1413

SUMMARY OF INVENTION

Technical Problem

In recent years, larger-scale culture for algae has been attempted, and it is assumed that a size of the culture pond becomes approximately several hectares to several hundred hectares. When a box-shaped lid is installed in the opening of such a vast culture pond by using the technology disclosed in Patent Document 1, only using the lid formed of resins may lead to insufficient strength. Therefore, it is necessary to install struts in the culture pond in order to support the box-shaped lid vertically from below.

In addition, a contact portion of the lid with respect to the strut needs strength enough to be supported by the strut. Thus, it is necessary to thicken a plate thickness of a plate-shaped member composing the lid to some extent, thereby causing a possibility of increased cost. Furthermore, the huge box-shaped thick lid used to cover the opening of the vast culture pond is increased in weight. Therefore, it is difficult to open and close the culture pond for maintenance or the like unless heavy machines are used.

The present invention is made in view of such circumstances, and aims to provide a culture device which can reduce the cost while ensuring the strength of a lid used to cover a culture pond, and enhance the maintainability thereof, by using a simple configuration.

Solution to Problem

According to a first aspect of the present invention, a culture device for culturing algae includes a culture pond including an opening on an upper side thereof, the culture pond accommodating an alga solution as a culture solution containing algae; a sheet having optical transparency and flexibility, the sheet sealing at least a portion of the opening of the culture pond; and a gas supply unit used to supply high concentration $CO_2$ gas having a higher concentration of carbon dioxide than that of the atmosphere, between the culture pond and the sheet. A gas storage space to store gas between a liquid surface of the alga solution and the sheet is formed by at least part of the supplied high concentration $CO_2$ gas.

According to a second aspect of the present invention, in the first aspect, the culture device further includes an outer groove formed along an outer periphery of the culture pond in an area different from the culture pond, the outer groove accommodating a liquid; and a holding unit arranged in the liquid accommodated in the outer groove, the holding unit holding an edge of the sheet in the liquid by vertically pulling the edge downward. The sheet and the liquid seal the opening of the culture pond over an entire area thereof by the holding unit vertically pulling the edge of the sheet downward in the liquid.

According to a third aspect of the present invention, in the second aspect, the holding unit allows the edge of the sheet to be detachably hooked thereto.

According to a fourth aspect of the present invention, in any one of the first to third aspects, the culture device further includes a concentration detection unit used to detect a concentration of carbon dioxide in the gas storage space. The gas supply unit is configured to supply the high concentration $CO_2$ gas when the concentration of the carbon dioxide detected by the concentration detection unit is less than a predetermined value.

According to a fifth aspect of the present invention, in any one of the first to fourth aspects, the gas supply unit is configured to supply the high concentration $CO_2$ gas into the alga solution. The high concentration $CO_2$ gas is released from the liquid surface of the alga solution after at least part of carbon dioxide contained in the high concentration $CO_2$ gas is dissolved into the alga solution.

According to a sixth aspect of the present invention, in any one of the first to fifth aspects, the culture device further includes a vibration applying unit configured to drop a droplet attached to the sheet by applying vibration to the sheet.

According to a seventh aspect of the present invention, in the sixth aspect, the culture device further includes an illuminance measurement unit used to measure illuminance of the gas storage space and illuminance of an outside space of the culture device. The vibration applying unit is configured to apply vibration to the sheet when a difference between the illuminance of the gas storage space and the illuminance of the outside space is equal to or more than a predetermined value.

According to an eighth aspect of the present invention, in any one of the first to seventh aspects, the culture device further includes a circulation flow channel used to supply gas which has been delivered outside of the culture device from the gas storage space, again into the gas storage space so as to circulate therein.

According to a ninth aspect of the present invention, a culture device for culturing algae includes a culture pond including an opening on an upper side thereof, the culture pond accommodating an alga solution as a culture solution containing algae; a sealing unit having optical transparency, the sealing unit being used to seal the opening of the culture pond; and an outer groove formed along an outer periphery of the culture pond in an area different from the culture pond, the outer groove accommodating a liquid. The sealing unit and the liquid seal the opening of the culture pond over an entire area thereof by holding an edge of the sealing unit in the liquid accommodated in the outer groove.

Effects of Invention

According to the present invention, a simple configuration can reduce the cost while ensuring the strength of a lid used to cover a culture pond, and enhance the maintainability thereof.

DESCRIPTION OF EMBODIMENTS

Hereinafter, preferred embodiments of the present invention will be described in detail with reference to the accompanying drawings. Dimensions, materials and the other specific numerical values in the embodiments are merely examples in order to facilitate understanding of the present invention, and do not limit the present invention unless otherwise described. In the description and the drawings, the same reference numerals are given to elements having substantially the same function and configuration, and the descriptions thereof will not be repeated here. In addition, the elements which do not directly relate to the present invention will not be illustrated. (First Embodiment)

Figure 1:
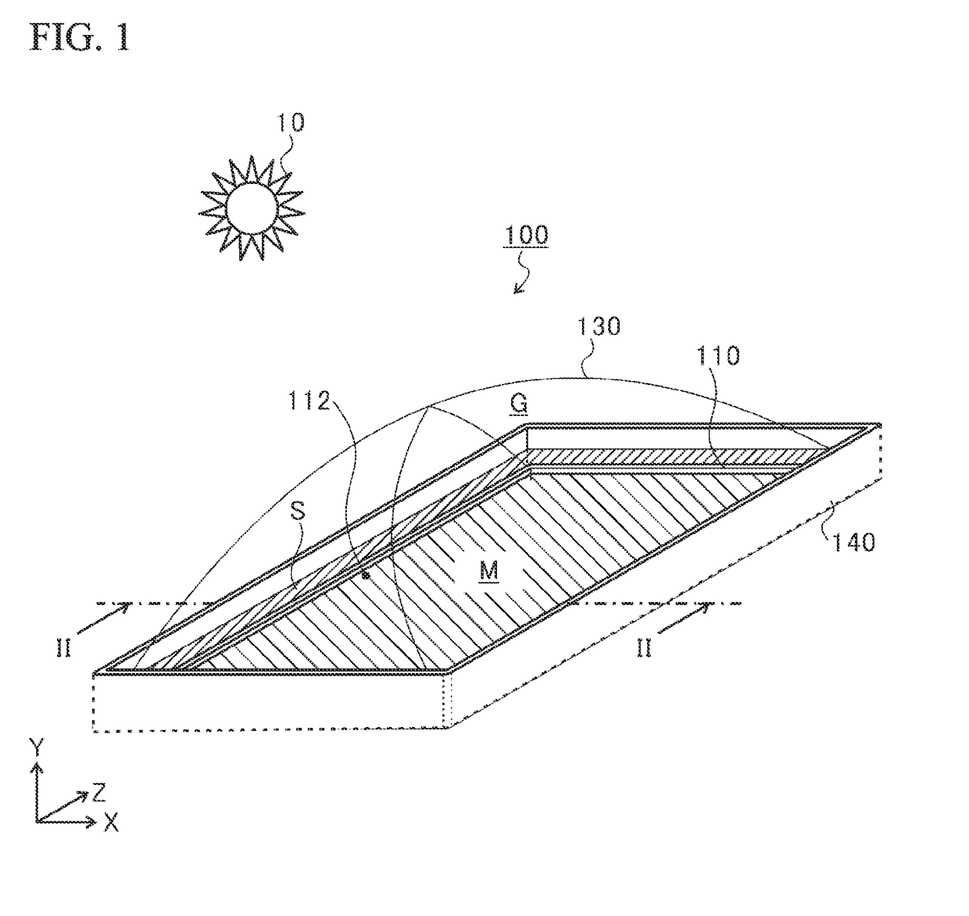
FIG. 1 is a perspective appearance view of a culture device according to a first embodiment of the present invention.
Figure 2:
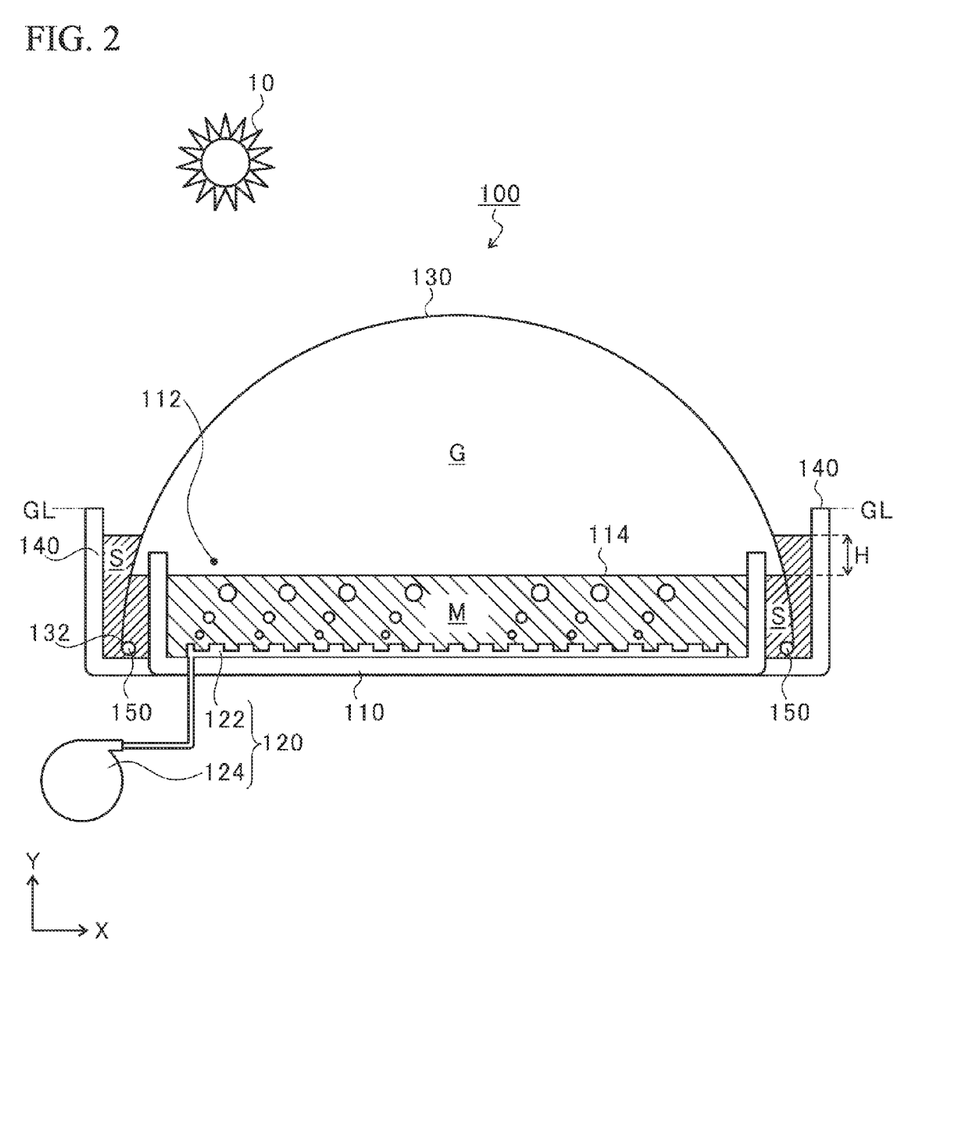
FIG. 2 is a cross-sectional view taken along a line II-II in FIG. 1.
Figure 3:
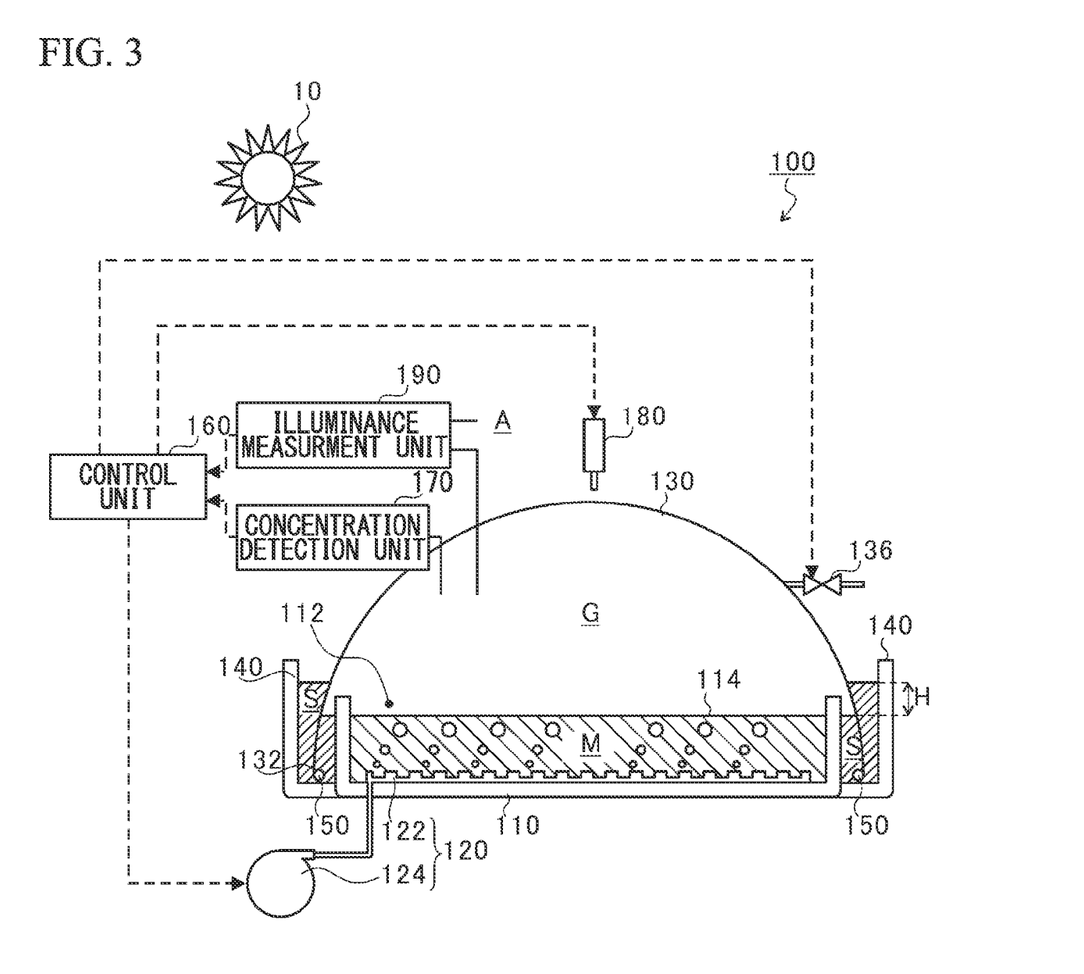
FIG. 3 is a functional block diagram to illustrate schematic functions of the culture device in the first embodiment of the present invention.

FIG. 1 is a perspective appearance view of a culture device 100 according to a first embodiment of the present invention; FIG. 2 is a cross-sectional view taken along the line II-II in FIG. 1; and FIG. 3 is a functional block diagram to illustrate schematic functions of the culture device 100. In addition, in FIG. 3, flow of a signal associated with a control is indicated by an arrow of a broken line.

As illustrated in FIGS. 1, 2 and 3, the culture device 100 is configured to include a culture pond 110; a gas supply unit 120; a sheet 130 (sealing unit); an outer groove 140; a holding unit 150; a control unit 160 (gas supply unit, vibration applying unit); a concentration detection unit 170; a vibration applying unit 180; and an illuminance measurement unit 190. In FIGS. 1 and 2, for convenience of illustration, the control unit 160, the concentration detection unit 170, the vibration applying unit 180 and the illuminance measurement unit 190 are not be illustrated.

The culture pond 110 includes an opening 112 on an upper side thereof and accommodates an alga solution M which is a culture solution containing algae. The culture pond 110 includes a bottom extending in a substantially horizontal direction and side walls extending upward from the edges of the bottom. In the present embodiment, the culture pond 110 is formed by digging the ground. Accordingly, the upper end of the culture pond 110 (upper end of the side walls) is arranged at a position lower than the ground level (indicated by GL in FIG. 2).

The gas supply unit 120 is configured to include a gas supply port 122 and a pump 124 (gas supply unit). The gas supply port 122 is configured to serve as a gas supplying member (for example, a porous member) disposed on a bottom surface inside the culture pond 110. The pump 124 delivers gas from a gas source (not illustrated) toward the culture pond 110. The gas supply port 122 and the pump 124 are connected to each other via a supply pipe.

The gas supply unit 120 supplies high concentration $CO_2$ gas (gas having a concentration of carbon dioxide which is higher than that of the atmosphere) from the gas source (not illustrated) into the alga solution M. In the present embodiment, the gas supply unit 120 intermittently supplies the high concentration $CO_2$ gas into the alga solution M in accordance with a control command from the control unit 160 (to be described below). In addition, when the culture device 100 starts to be operated, the gas supply unit 120 supplies the high concentration $CO_2$ gas containing the carbon dioxide of approximately 10%, and stops supply of the high concentration $CO_2$ gas if the pressure in a gas storage space G (to be described below) becomes equal to a predetermined value P.

During an operation of the culture device 100, the gas supply unit 120 supplies the high concentration $CO_2$ gas containing the carbon dioxide of approximately 10% into the alga solution M in accordance with the control command from the control unit 160. A supply process of the gas supply unit 120 using the control unit 160 will be described in detail below.

When culturing the algae, in a case where the alga solution M is not circulated inside the culture pond 110, the algae are precipitated in the culture solution to form a cluster of the algae, and photosynthetic efficiency or consumption efficiency of the culture solution is deteriorated, whereby overall culture efficiency may be decreased. In the present embodiment, the gas supply unit 120 supplies the high concentration $CO_2$ gas into the alga solution M through bubbling supply or the like in which the gas is supplied into the liquid. Therefore, it is possible to stir the alga solution M with the high concentration $CO_2$ gas. In this manner, it is possible to suppress a decrease in the photosynthetic efficiency or a decrease in the consumption efficiency of the culture solution due to the precipitation of the algae.

The high concentration $CO_2$ gas supplied into the alga solution M by the gas supply unit 120 is released from a liquid surface 114 of the alga solution M after at least part of the carbon dioxide contained in the high concentration $CO_2$ gas is dissolved into the alga solution M.

The sheet 130 is a member formed in a sheet shape which has optical transparency and flexibility (preferably, formed of resins resistant to ultraviolet irradiation, for example, polyvinyl chloride, polyethylene, polypropylene or the like). The sheet 130 is formed so as to have a size which can sufficiently cover the opening 112 of the culture pond 110. That is, the sheet 130 is a member to entirely seal the opening 112 of the culture pond 110. In addition, during the operation of the culture device 100, the gas supply unit 120 supplies the high concentration $CO_2$ gas to the inside of the sheet 130, that is, to between the culture pond 110 and the sheet 130. Since the sheet 130 is expanded by the gas supply, the sheet 130 is formed so as to have a proper size in view of the expansion. As illustrated in FIG. 2, the edge 132 of the sheet 130 is held inside a liquid S accommodated in the outer groove 140 by the holding unit 150 (to be described later). In this manner, the sheet 130 and the liquid S seal the opening 112 over the entire area thereof.

Part of the carbon dioxide contained in the high concentration $CO_2$ gas which has been supplied into the alga solution M by the gas supply unit 120 is released from the liquid surface 114 without being dissolved into the alga solution M while the gas moves in the alga solution M to the liquid surface 114. However, since the sheet 130 seals the opening 112 of the culture pond 110, the gas containing the carbon dioxide which has been released from the liquid surface 114 remains inside the sheet 130 to form the gas storage space G. That is, at least part of the supplied high concentration $CO_2$ gas forms the gas storage space G between the liquid surface 114 and the sheet 130. Therefore, it is possible to prevent the carbon dioxide discharged from the liquid surface 114 from being released to the atmosphere (atmosphere outside the culture device 100, the same below).

The concentration of the carbon dioxide of the gas stored in the gas storage space G is higher than that of the atmosphere. As described above, the concentration of the carbon dioxide dissolved into the alga solution M varies until the concentration reaches equilibrium with a concentration of the carbon dioxide in a gaseous phase of the gas storage space G. Accordingly, it is possible to maintain a higher concentration of the carbon dioxide dissolved into the alga solution M than that of the atmosphere. In addition, even if the concentration of the carbon dioxide dissolved into the alga solution M is decreased due to the consumption of the carbon dioxide by the algae, since the alga solution M maintains a state of contacting the gas storage space G having a high concentration of the carbon dioxide, it is possible to dissolve the carbon dioxide inside the gas storage space G into the alga solution M.

In addition, as described above, since the sheet 130 has the flexibility, if an inside pressure thereof is increased, the sheet 130 can swell upward. If the gas supply unit 120 supplies the high concentration $CO_2$ gas so that a pressure P (gauge pressure) of the gas storage space G becomes a pressure equal to or greater than a weight ($g/cm^2$) of the sheet 130 per unit area, the high concentration $CO_2$ gas causes the sheet 130 to swell and the gas storage space G is formed. That is, it is possible to support the sheet 130 from inside (below) using the gas supplied by the gas supply unit 120.

In this manner, using a simple configuration in which the sheet 130 is composed of a member with flexibility and the gas supply unit 120 supplies the high concentration $CO_2$ gas to the inside of the sheet 130, it is possible to form the gas storage space G and to cover the opening 112 with the sheet 130 without using struts or the like to support the sheet 130. In addition, it is possible to form the sheet 130 having a function as a lid used to seal the opening 112 by using a member with a thin thickness (for example, approximately 0.1 mm). Therefore, as compared to a case of forming the lid using a plate-shaped resin, it is possible to achieve weight reduction and to improve convenience. Consequently, it is possible to easily open and close the culture pond 110 during the maintenance thereof.

Furthermore, as described above, the sheet 130 is formed of the member having optical transparency. Accordingly, even if the whole area of the opening 112 is sealed with the sheet 130, the light from the sun 10 or the like sufficiently enters the alga solution M through the opening 112.

In addition, a discharge valve 136 is attached to the sheet 130 in order to discharge the gas into the outside from the inside of the sheet 130.

The outer groove 140 is formed in an area different from the culture pond 110 and accommodates a liquid. Similar to the culture pond 110, the outer groove 140 also includes a bottom and side walls extending upward from the edges of the bottom. As illustrated in FIG. 1, in the present embodiment, the outer groove 140 is formed along the outer periphery of the culture pond 110. That is, the side walls of the outer groove 140 are arranged so as to surround the side walls of the culture pond 110 in a plan view. The inside of the outer groove 140 (space between the side walls of the outer groove 140 and the side walls of the culture pond 110) accommodates the liquid S having sterilizing effect (for example, aqueous solution containing hypochlorite). In the present embodiment, the outer groove 140 is formed by digging the ground, and the upper end of the outer groove 140 (upper end of the side walls) is arranged at a position substantially equal to the ground level (indicated by GL in FIG. 2).

For example, the holding unit 150 is formed in a frame shape encircling the outer periphery of the culture pond 110 by using a metal, and is arranged so as to be submerged in the liquid S of the outer groove 140. In the liquid S accommodated in the outer groove 140, the holding unit 150 pulls the edge 132 of the sheet 130 vertically downward and holds the edge 132 in the liquid S.

To describe in detail, force is applied to the sheet 130 in an expanding direction by the pressure P of the gas storage space G formed inside the sheet 130, and a vertical component of the force becomes a buoyancy F. If the weight of the holding unit 150 is set to be a weight which allows the edge 132 to be pulled vertically downward by using force equal to or greater than the buoyancy F, it is possible to hold the edge 132 in the liquid S. In the present embodiment, the level of the liquid surface of the liquid S at the inside (near the culture pond 110) of the holding unit 150 (sheet 130) is substantially equal to the level of the liquid surface 114. In addition, the liquid surface of the liquid S at the outside of the holding unit 150 (sheet 130) is located higher than the level of the liquid surface at the inside thereof by a pressure head (indicated by H in FIG. 2) corresponding to the buoyancy F.

According to the above-described configuration, the edge 132 of the sheet 130 is held in the liquid S over the entire periphery thereof. Therefore, the sheet 130 and the liquid S can reliably seal the opening 112 of the culture pond 110 over the entire area thereof.

In addition, since the opening 112 is sealed with the sheet 130 and the liquid S over the entire area, external microorganisms may pass through the liquid S and may enter the culture pond 110. Therefore, it is possible to sterilize the microorganisms entering from outside by arranging the liquid S to be a liquid having a sterilizing effect (effect of killing the microorganisms). Consequently, it is possible to prevent contaminants from entering the alga solution M (contamination of the alga solution M).

In addition, in the present embodiment, the holding unit 150 is configured to allow the edge 132 of the sheet 130 to be detachably hooked thereto.

Figure 4A:
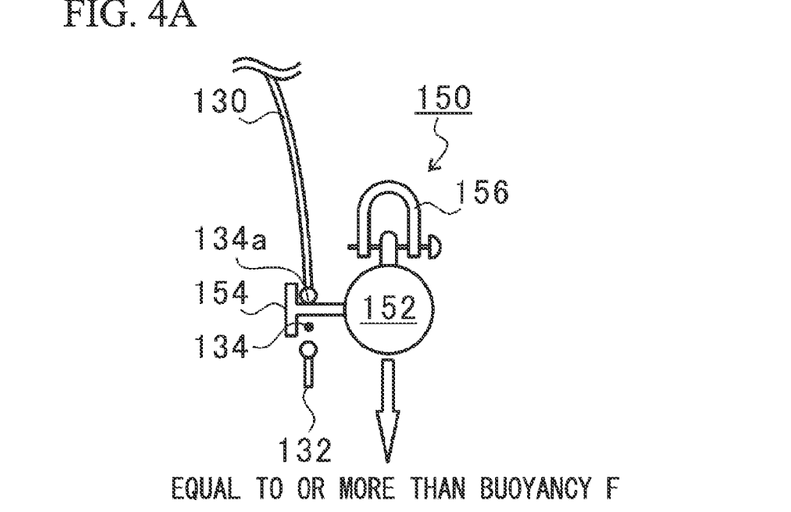
FIG. 4A is a cross-sectional view illustrating an example of a specific configuration of a holding unit.
Figure 4B:
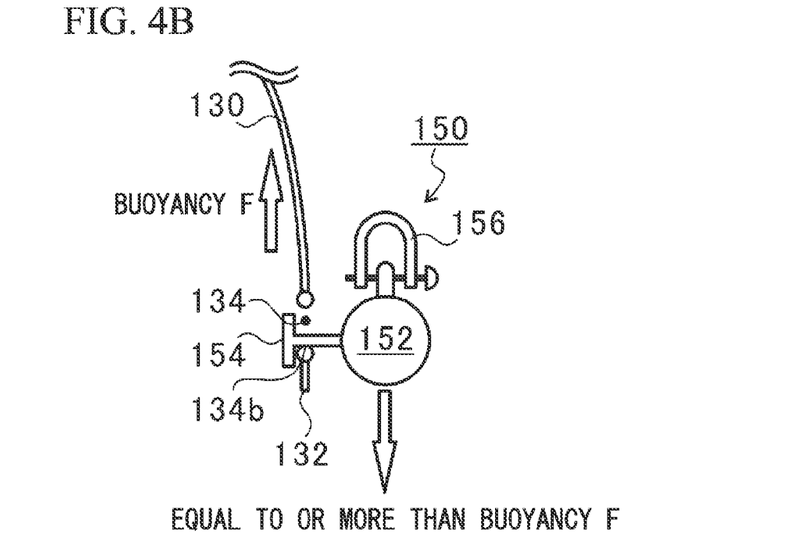
FIG. 4B is an explanatory view to illustrate a case where a sheet is pulled by the holding unit.

FIG. 4A is a cross-sectional view showing an example of a specific configuration of the holding unit 150, and FIG. 4B is an explanatory view showing a case where the sheet 130 is pulled by the holding unit 150. In the present embodiment, engagement holes 134 are formed in the sheet 130 in the vicinity of the edge 132. The engagement holes 134 are disposed along the outer periphery of the sheet 130 at, for example, substantially regular intervals.

On the other hand, as illustrated in FIG. 4A, the holding unit 150 is configured to include a main body frame 152, engagement hooks 154, and a lifting portion 156.

The main body frame 152 is formed so as to encircle the outer periphery of the culture pond 110. The engagement hooks 154 are composed of rivets and the like, and are provided in the main body frame 152. The engagement hooks 154 can be engaged with the engagement holes 134 provided in the sheet 130. The engagement hooks 154 are set so as to have dimensions which can be engaged with the engagement holes 134 corresponding thereto. The lifting portion 156 is composed of an I-bolt and the like, and lifting portions 156 are provided in the main body frame 152. The lifting portions 156 are hooked and lifted up by a crane or the like, and thus, the entire holding unit 150 is lifted up.

When the sheet 130 is installed in the culture pond 110, the lifting portions 156 are first hooked and lifted up by the crane or the like. Then, the main body frame 152 is submerged and installed in the liquid S accommodated in the outer groove 140. Subsequently, the engagement holes 134 of the sheet 130 are engaged with the engagement hooks 154 of the holding unit 150. In this manner, as illustrated in FIG. 4A, an edge 134a positioned vertically above the engagement hole 134 is hooked to the engagement hook 154. Consequently, the opening 112 is sealed with the sheet 130 and the liquid S over the entire area thereof.

When the high concentration $CO_2$ gas is supplied into the alga solution M by the gas supply unit 120, the gas storage space G having the pressure P is formed between the liquid surface 114 and the sheet 130. Therefore, as illustrated in FIG. 4B, the pressure P of the gas storage space G generates the buoyancy F in the sheet 130, and an edge 134b positioned vertically below the engagement hole 134 is hooked to the engagement hook 154.

The holding unit 150 is set to have the weight which allows the edge 132 to be pulled vertically downward by using the force equal to or greater than the buoyancy F. Accordingly, it is possible to hold the edge 132 in the liquid S against the buoyancy F.

As described above, since the holding unit 150 is simply configured to be hooked to the sheet 130, the sheet 130 can be easily attached to and detached from the holding unit 150. Therefore, when the sheet 130 is damaged or deteriorated due to outside air, ultraviolet irradiation or the like, the sheet 130 can be easily replaced.

Referring back to FIG. 3, the control unit 160 includes a central processing unit (CPU), a ROM in which programs are stored, and a semiconductor integrated circuit having a RAM and the like as a work area, and manages and controls the culture device 100.

Based on a concentration signal (to be described below) transmitted from the concentration detection unit 170, the control unit 160 controls an operation of the pump 124 and an opening degree of the discharge valve 136 (valve to discharge the gas outward from the inside of the sheet 130) (gas supply process). In addition, based on an illuminance signal (to be described below) transmitted from the illuminance measurement unit 190, the control unit 160 controls the vibration applying unit 180 (vibration applying process). The gas supply process and the vibration applying process using the control unit 160 will be described below in detail.

The concentration detection unit 170 detects a concentration of the carbon dioxide in the gas storage space G and transmits the concentration signal which is a signal indicating the detected concentration to the control unit 160.

The control unit 160 receives the concentration signal, and when the concentration of the carbon dioxide which is indicated by the received concentration signal is less than a predetermined value (for example, 2%), the control unit 160 performs the gas supply process. To be more specific, the algae consume the carbon dioxide and produce oxygen when performing the photosynthesis. As described above, since the opening 112 in the culture device 100 is sealed with the sheet 130, if the algae continue to perform the photosynthesis, the concentration of the carbon dioxide dissolved into the alga solution M is decreased, and the carbon dioxide in the gas storage space G is dissolved into the alga solution M. In addition, the oxygen produced by the algae is released from the alga solution M to the gas storage space G. Therefore, the concentration of the carbon dioxide in the gas storage space G is decreased and in contrast, the concentration of the oxygen therein is increased.

The control unit 160, if the concentration of the carbon dioxide which is indicated by the concentration signal is less than the predetermined value (for example, 2%), first adjusts the opening degree of the discharge valve 136 and discharges the gas corresponding to 50% of capacity of the gas storage space G into the outside of the sheet 130. Subsequently, the control unit 160 drives the pump 124 of the gas supply unit 120 and supplies the high concentration $CO_2$ gas having approximately 10% of the concentration of the carbon dioxide into the alga solution M until the pressure of the gas storage space G becomes equal to the pressure P. In this manner, it is possible to increase the concentration of the carbon dioxide in the gas storage space G as compared to the concentration before the gas supply process is performed. For example, the concentration can be increased up to 6%.

As described above, if the concentration of the carbon dioxide in the gas storage space G is decreased due to the consumption of the carbon dioxide during the photosynthesis of the algae, the control unit 160 uses the gas supply unit 120 to supply new high concentration $CO_2$ gas into the alga solution M. Therefore, it is possible to maintain the concentration of the carbon dioxide in the gas storage space G to have the predetermined value. As a result, the concentration of the carbon dioxide dissolved in the alga solution M can also be maintained to have the predetermined value. Accordingly, it is possible to maintain a high photosynthetic efficiency of the algae.

The vibration applying unit 180 is composed of an air gun, a vibrator, or the like which is installed near the sheet 130, and can apply vibrations to the sheet 130 in accordance with a control command from the control unit 160.

As described above, in the culture device 100, since the opening 112 is sealed with the sheet 130, if the culture of the algae is continued, water vapor evaporated from the alga solution M may be condensed inside the sheet 130 and the water vapor may become droplets to be attached to an inner surface of the sheet 130. In this case, the light incidence from the outside of the sheet 130 to the inside thereof may be blocked by the droplets, and thereby a reaching efficiency of the light to the alga solution M may be decreased.

In the above-described case, the vibration applying unit 180 applies vibrations to the sheet 130 to drop the droplets attached to the inner surface of the sheet 130 to the culture pond 110. In this manner, it is possible to remove the droplets from the inner surface of the sheet 130. The droplets may be dropped to the outer groove 140. In this manner, it is possible to prevent a light transmission efficiency of the sheet 130 from being decreased due to the droplets.

In addition, even when droplets are attached to an outer surface of the sheet 130, the vibration applying unit 180 applies vibrations to the sheet 130 and thereby can drop the droplets attached to the outer surface of the sheet 130 to the outside (such as the outer groove 140) of the sheet 130. As a result, the droplets can be removed from the sheet 130.

The illuminance measurement unit 190 measures the illuminance of the gas storage space G and the illuminance of an outside space A of the sheet 130 (outside space of the culture device 100), and transmits the illuminance signal which is the signal indicating the measured illuminance, to the control unit 160. The control unit 160 receives the illuminance signal and performs the vibration applying process when a difference between the illuminance of the gas storage space G and the illuminance of the outside space A of the sheet 130 which are indicated by the received illuminance signal is equal to or more than a predetermined threshold value (predetermined value). As described above, if the water vapor or the like evaporated from the alga solution M is condensed to be the droplets which are attached to an inner surface of the sheet 130, the droplets may block the light incidence. In other words, the illuminance of the gas storage space G is decreased.

In the above-described case, when the difference between the illuminance of the gas storage space G and the illuminance of the outside space A of the sheet 130 is equal to or more than the predetermined threshold value, that is, when the gas storage space G is darker than the outside space A, the control unit 160 considers that the droplets are attached to the sheet 130, and drives the vibration applying unit 180 to apply vibrations to the sheet 130. Therefore, the droplets are removed from the sheet 130, thereby enabling the sheet 130 to maintain the original light transmission efficiency thereof.

In addition, the control unit 160 calculates a difference between the illuminance of the gas storage space G and the illuminance of the outside space A of the sheet 130. Accordingly, in a case where only weather such as cloudy causes the illuminance of the gas storage space G to be decreased, it is possible to avoid erroneous determination that the droplets are attached to the inner surface of the sheet 130 even though the droplets are not attached thereto. Therefore, it is possible to avoid a situation where the vibration applying unit 180 unnecessarily applies vibrations.

As described above, according to the culture device 100 of the present embodiment, the opening 112 of the culture pond 110 is covered with the sheet 130 having flexibility, and the high concentration $CO_2$ gas is allowed to be stored inside the sheet 130. Therefore, the high concentration $CO_2$ gas can reliably support the sheet 130 from inside without using struts.

In addition, the sheet 130 having a function of the lid used to cover the opening 112 is a thin member. Therefore, as compared to a case where the lid is composed of a plate-shaped member, it is possible to significantly reduce the thickness thereof, thereby achieving weight reduction of the lid. Accordingly, as compared to the case where the lid is composed of the plate-shaped member, it is possible to reduce the cost for the struts and the cost for materials used as the lid.

Furthermore, as compared to a case where the lid is composed of the plate-shaped member, the sheet 130 is very light. Therefore, it is possible to easily open and close the culture device 100, thereby improving the maintainability thereof (Second Embodiment)

Figure 5:
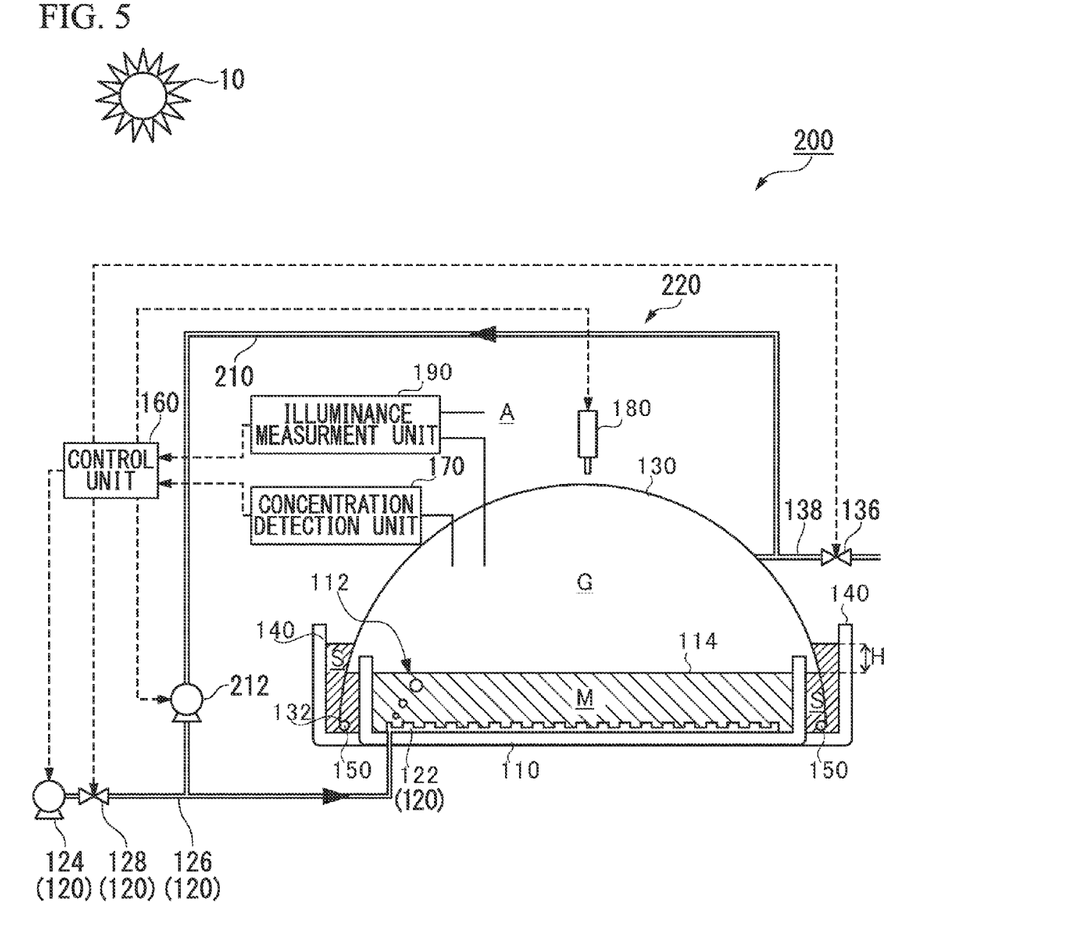
FIG. 5 is a functional block diagram to illustrate schematic functions of a culture device according to a second embodiment of the present invention.

Referring to FIG. 5, a culture device according to a second embodiment of the present invention will be described. FIG. 5 is a functional block diagram to illustrate schematic functions of a culture device 200 in the second embodiment of the present invention. In the following description, the same reference numerals are given to the elements the same as the configuring elements of the first embodiment, and descriptions thereof may be omitted here.

The gas supply unit 120 includes the gas supply port 122, the pump 124, a supply pipe 126, and a supply stop valve 128. The supply pipe 126 connects the gas supply port 122 and the pump 124. The high concentration $CO_2$ gas delivered from the pump 124 is supplied into the alga solution M through the supply pipe 126 and the gas supply port 122. The supply stop valve 128 is provided in the supply pipe 126, and can open and close a flow channel of the supply pipe 126 based on a control command from the control unit 160.

The sheet 130 and the discharge valve 136 are connected to each other through a discharge pipe 138. That is, the discharge pipe 138 causes the gas storage space G inside the sheet 130 and the discharge valve 136 to communicate with each other. The discharge valve 136 can open and close a flow channel of the discharge pipe 138 based on a control command from the control unit 160.

In the present embodiment, a circulation pipe 210 connecting the supply pipe 126 and the discharge pipe 138 is provided. One end of the circulation pipe 210 is connected to the supply pipe 126 positioned between the supply stop valve 128 and the gas supply port 122, and the other end of the circulation pipe 210 is connected to the discharge pipe 138 positioned between the sheet 130 and the discharge valve 136. That is, in the culture device 200, a circulation flow channel 220 is formed of a partial flow channel of the discharge pipe 138, the circulation pipe 210 and a partial flow channel of the supply pipe 126. The circulation flow channel 220 is a flow channel used to supply the gas which has been delivered to the outside of the culture device 200 from the gas storage space G, again into the gas storage space G so as to circulate therein.

A second pump 212 (gas supply unit) is provided in the circulation pipe 210 (in the present embodiment, near the supply pipe 126). The second pump 212 can supply the gas in the circulation pipe 210 or the supply pipe 126 toward the gas storage space G even in a state where the pump 124 is not operated. In addition, an operation of the second pump 212 is controlled based on a control command from the control unit 160.

Next, an operation of the culture device 200 according to the present embodiment will be described.

If the control unit 160 and the concentration detection unit 170 are configured to be the same as those of the first embodiment, when the concentration of the carbon dioxide of the gas storage space G is less than the predetermined value, the control unit 160 determines that the carbon dioxide is insufficient in the gas storage space G. Accordingly, the pump 124 is operated based on a control command from the control unit 160. In this case, since the second pump 212 is provided in the circulation pipe 210 in the present embodiment, the second pump 212 can prevent the high concentration $CO_2$ gas from flowing toward the discharge valve 136 through the circulation pipe 210 without passing through the gas storage space G.

On the other hand, when the concentration of the carbon dioxide of the gas storage space G is equal to or more than the predetermined value, the control unit 160 determines that the sufficient carbon dioxide is stored inside the gas storage space G. Accordingly, the operation of the pump 124 is stopped based on a control command from the control unit 160.

As described above, if the carbon dioxide in the alga solution M is consumed due to the photosynthesis of the algae, the carbon dioxide inside the gas storage space G is dissolved into the alga solution M. However, in a state where the pump 124 is stopped, the carbon dioxide inside the gas storage space G is dissolved into the alga solution M only via the liquid surface 114. Therefore, it may be difficult to quickly dissolve the carbon dioxide therein.

In the present embodiment, if it is determined that the concentration of the carbon dioxide of the gas storage space G is equal to or more than the predetermined value by the detection of the concentration detection unit 170, the control unit 160 operates the second pump 212 in a state where the supply stop valve 128 and the discharge valve 136 are closed. The operation of the second pump 212 causes the gas in the circulation pipe 210 and in the supply pipe 126 to flow toward the gas storage space G. Furthermore, in the state where the supply stop valve 128 and the discharge valve 136 are closed, the circulation flow channel 220 of a closed loop is formed. Therefore, the operation of the second pump 212 causes the gas to flow in the circulation flow channel 220 in the same direction.

It is determined that the concentration of the carbon dioxide of the gas storage space G is equal to or more than the predetermined value by the detection of the concentration detection unit 170. Accordingly, the sufficient carbon dioxide is still present in the gas storage space G. Such gas inside the gas storage space G is re-supplied into the alga solution M via the circulation flow channel 220. Therefore, it is possible to quickly dissolve the carbon dioxide into the alga solution M.

As a result, according to the present embodiment, even in a state where the pump 124 is stopped, it is possible to ensure the high concentration of the carbon dioxide in the alga solution M, and thus to maintain an environment suitable for the photosynthesis of the algae inside the culture pond 110.

Hereinbefore, the preferred embodiments of the present invention have been described with reference to the accompanying drawings. However, the present invention is not limited to the above embodiments, but is limited only by the scope of the appended claims. Each configuration or each operation mode described in the above-described embodiments is an example, and the configuration can be subjected to additions, omissions, substitutions and the other modifications without departing from the gist of the present invention. These modifications are of course within the technical scope of the present invention.

For example, in the above-described embodiments, the edge 132 of the sheet 130 is held in the liquid S by the holding unit 150, and the sheet 130 and the liquid S seal the opening 112 of the culture pond 110 over the entire area. However, when culturing the algae which are strong against disturbance such as contamination, it is not always necessary to seal the opening 112 over the entire area. In this case, if the sheet 130 seals at least a portion of the opening 112, the carbon dioxide released from the liquid surface 114 can be stored inside the sheet 130, and thus, it is possible to improve a dissolving efficiency of the carbon dioxide into the alga solution M. For example, the holding unit 150 is arranged along an inner periphery of the culture pond 110 and the holding unit 150 is installed so as to be submerged inside the culture pond 110, whereby the sheet 130 may cover at least a portion of the opening 112. In this case, the outer groove 140 may not be provided.

In the above-described embodiments, the gas supply unit 120 supplies the high concentration $CO_2$ gas into the alga solution M. However, since it is sufficient if the gas storage space G is formed inside the sheet 130, the gas supply unit 120 may supply the high concentration $CO_2$ gas to the inside of the sheet 130 without passing through the alga solution M.

In the above-described embodiments, in the configuration illustrated in FIGS. 4A and 4B, the main body frame 152 is installed outside the sheet 130. However, the main body frame 152 may be installed inside the sheet 130. In this case, the lifting portion 156 may be provided in the main body frame 152 at a position opposite to a position at which the engagement hook 154 is connected to the main body frame 152.

In the above-described embodiments, based on the measurement result of the illuminance measurement unit 190, the vibration applying unit 180 applies vibrations to the sheet 130. However, without using the illuminance measurement unit 190, the vibration applying unit 180 may apply vibrations to the sheet 130 periodically for every predetermined time by, for example, using a timer or the like.

The shape of the lid (sealing unit) used to seal the opening 112 is not limited to the sheet shape, and the sealing unit may be formed of a member having no flexibility. In any case, if the edge of the sealing unit is configured to be held in the liquid accommodated in the outer groove, the sealing unit and the liquid can seal the opening of the culture pond over the entire area thereof and thus, it is possible to prevent the contaminants from entering from outside.

INDUSTRIAL APPLICABILITY

The present invention can be applied to a culture device which cultures algae or the like.

REFERENCE SIGNS LIST

G Gas storage space
M Alga solution
S Liquid
100, 200 Culture device
110 Culture pond
112 Opening
114 Liquid surface
124 Pump (gas supply unit)
130 Sheet (sealing unit)
132 Edge
140 Outer groove
150 Holding unit
160 Control unit (gas supply unit, vibration applying unit)
170 Concentration detection unit
180 Vibration applying unit
190 Illuminance measurement unit
212 Second pump (gas supply unit)
220 Circulation flow channel

The invention claimed is:

1. A culture device for culturing algae, comprising:
a culture pond including an opening on an upper side thereof, the culture pond accommodating an alga solution as a culture solution containing algae;
a sheet having optical transparency and flexibility, the sheet sealing at least a portion of the opening of the culture pond;
a gas supplier configured to supply high concentration $CO_2$ gas having a higher concentration of carbon dioxide than that of the atmosphere, between the culture pond and the sheet;
an outer groove formed along an outer periphery of the culture pond in an area different from the culture pond, the outer groove accommodating a liquid; and
a frame connected to an edge of the sheet and arranged in the liquid accommodated in the outer groove;
wherein a gas storage space to store gas between a liquid surface of the alga solution and the sheet is formed by at least part of the supplied high concentration $CO_2$ gas, and
wherein the frame and the edge of the sheet are arranged in the liquid accommodated in the outer groove, and the sheet and the liquid seal the opening of the culture pond on the entire area thereof.

2. The culture device according to claim 1, wherein the frame allows the edge of the sheet to be detachably hooked thereto.

3. The culture device according to claim 1, further comprising:
a concentration detector configured to detect a concentration of carbon dioxide in the gas storage space,
wherein the gas supplier is configured to supply the high concentration $CO_2$ gas when the concentration of the carbon dioxide detected by the concentration detector is less than a predetermined value.

4. The culture device according to claim 1, wherein the gas supplier is configured to supply the high concentration $CO_2$ gas into the alga solution, and
wherein the high concentration $CO_2$ gas is released from the liquid surface of the alga solution after at least part of carbon dioxide contained in the high concentration $CO_2$ gas is dissolved into the alga solution.

5. The culture device according to claim 1, further comprising:
a vibrator disposed facing the sheet and configured to apply vibration to the sheet.

6. The culture device according to claim 5, further comprising:
an illuminance sensor configured to measure illuminance of the gas storage space and illuminance of an outside space of the culture device,
wherein the vibrator is configured to apply vibration to the sheet when a difference between the illuminance of the gas storage space and the illuminance of the outside space is equal to or more than a predetermined value.

7. The culture device according to claim 1, further comprising:
a circulation flow channel used to supply gas which has been delivered outside of the culture device from the gas storage space, again into the gas storage space so as to circulate therein.

* * * * *